United States Patent [19]
Rae et al.

[11] Patent Number: 5,935,974
[45] Date of Patent: Aug. 10, 1999

[54] DIPHENYLMETHYLENE PIPERIDINE DERIVATIVES

[75] Inventors: Duncan Robertson Rae, Lanark; David Robert Jaap, Glasgow, both of United Kingdom

[73] Assignee: Akzo Nobel, N.V., Arnhem, Netherlands

[21] Appl. No.: 08/983,059

[22] PCT Filed: Jul. 9, 1996

[86] PCT No.: PCT/EP96/03099

§ 371 Date: Jan. 7, 1998

§ 102(e) Date: Jan. 7, 1998

[87] PCT Pub. No.: WO97/03065

PCT Pub. Date: Jan. 30, 1997

[30] Foreign Application Priority Data

Jul. 12, 1995 [EP] European Pat. Off. .............. 95201910

[51] Int. Cl.⁶ ........................ A61K 31/445; C07D 401/06
[52] U.S. Cl. .......................... 514/326; 514/316; 546/187; 546/189; 546/191; 546/208
[58] Field of Search .................... 546/187, 189, 546/191, 208; 514/316, 326

[56] References Cited

U.S. PATENT DOCUMENTS 3,922,276  11/1975  Duncan et al. ..................... 546/226
4,180,583  12/1979  Carr et al. ............................. 514/317
4,540,780   9/1985  Downs et al. ........................ 544/129
4,666,905   5/1987  Downs .................................. 514/222

*Primary Examiner*—Ceila Chang
*Attorney, Agent, or Firm*—Michael G. Sullivan

[57] ABSTRACT

The invention relates to a diphenylmethylene piperidine derivative of the formula

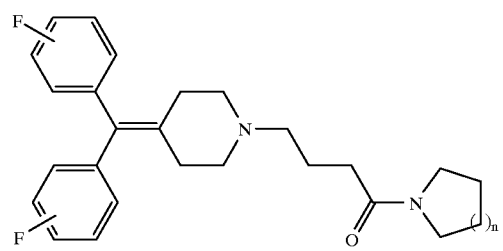

wherein n is 1 or 2; or a pharmaceutically acceptable salt thereof, for use in therapy, in particular for use as a dopamine antagonist for the treatment or prophylaxis of psychotic disorders.

7 Claims, No Drawings

DIPHENYLMETHYLENE PIPERIDINE DERIVATIVES

This application is a 371 of PCT/EP96/03099 filed Jul. 9, 1996.

FIELD OF THE INVENTION

The invention relates to diphenylmethylene piperidine derivatives, pharmaceutical compositions containing the same, a method of production thereof, and a method of treatment and prophylaxis of psychotic disorders.

BACKGROUND OF THE INVENTION

Related diphenylmethylene piperidine derivatives are known in the art. Notably, related compounds are disclosed in U.S. Pat. No. 4,540,780, and in a divisional thereof U.S. Pat. No. 4,666,905, mentioning diphenylmethylene piperidine derivatives which are useful as anti-emetic, anti-histamine, pulmonary, and antispasmodic agents.

SUMMARY OF THE INVENTION

The present invention relates to diphenylmethylene piperidine derivatives of the formula

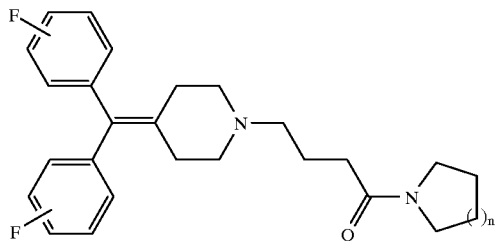

wherein n is 1 or 2; or a pharmaceutically acceptable salt thereof.

With more preference the diphenylmethylene piperidine derivatives of the invention have both fluorine atoms attached to the para position of the benzene rings.

A preferred compound is the diphenylmethylene piperidine derivative having the formula

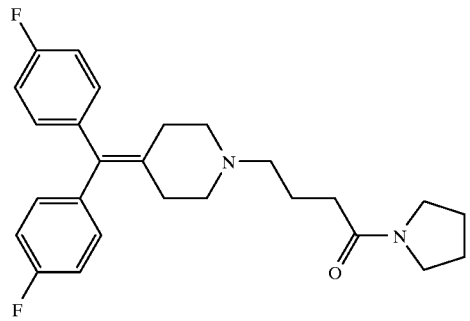

or a pharmaceutically acceptable salt thereof.

DETAILED DESCRIPTION OF THE INVENTION

The diphenylmethylene piperidine derivatives of the invention are dopamine receptor antagonists which have strong antipsychotic activity, as is demonstrated in vivo in the apomorphine climbing test (ACT). The ability of dopamine receptor antagonists to inhibit the behavioural effects in rodents caused by dopamine agonists such as apomorphine is a well established criterion for predicting the antipsychotic efficacy of these drugs in man (see e.g. W. C. Bowman and M. J. Rand, Textbook of Pharmacology, 2nd ed., 1980, 15, 6). A particularly relevant test in this respect is the ACT which measures the ability of a dopamine antagonist to inhibit the climbing behaviour in mice, induced by the subcutaneous administration of apomorphine. Activity in this test has been widely used as a predictor of antipsychotic activity i.e anti-schizophrenic activity (see e.g. J. T. Strupczewski et al., J. Med. Chem., 1995, 38, 1119).

The compounds of this invention (entries 1 and 2) were compared with various related diphenylmethylene piperidine derivatives according to U.S. Pat. No. 4,540,780 (entries 3–15), and results are given in the following table:

TABLE I

| Entry | $R_1$ | m | X | Y | n | $R_2$ | ACT (sc) |
|---|---|---|---|---|---|---|---|
| THIS INVENTION | | | | | | | |
| 1 | F | 3 | O | C | 1 | H | 0.5 |
| 2 | F | 3 | O | C | 2 | H | 0.5 |
| COMPOUNDS ACCORDING TO U.S. Pat. No. 4,540,780 | | | | | | | |
| 3 | H | 3 | O | C | 1 | H | 2.1 |
| 4 | H | 3 | O | C | 2 | H | 1.1 |
| 5 | F | 4 | O | C | 1 | H | 3.7 |
| 6 | H | 2 | O | C | 2 | H | >22 |
| 7 | H | 4 | O | C | 2 | H | 3.6 |
| 8 | H | 5 | O | C | 2 | H | 7.4 |
| 9 | H | 3 | O | O | 2 | H | 5 |
| 10 | F | 3 | O | C | 2 | OH | 6.8 |
| 11 | H | 4 | O | C | 2 | $(CH_3)_2$ | >22 |
| 12 | H | 3 | O | C | 2 | $(CH_3)_2$ | >22 |
| 13 | F | 3 | $H_2$ | C | 2 | H | >22 |
| 14 | H | 3 | $H_2$ | C | 1 | H | >22 |
| 15 | H | 3 | $H_2$ | C | 2 | H | >22 |

The five compounds of Table I which have the highest activity after subcutaneous administration, were tested in the ACT after oral administration. The results are given in Table II.

TABLE II

| Entry | ACT (sc) | ACT (po) |
|---|---|---|
| 1 | 0.5 | 2.8 |
| 2 | 0.5 | 1.4 |
| 3 | 2.1 | 47 |
| 4 | 1.1 | 22 |
| 7 | 3.6 | 33.8 |

As demonstrated in Table II, the compounds of this invention have good oral activity in comparison with the diphenylmethylene piperidine derivatives according to U.S. Pat. No. 4,540,780. Moreover, the instantly claimed compounds do not exhibit catalepsy, which predicts that they are devoid of unwanted extrapyramidal side effects.

The compounds of the invention can be prepared by methods known in the art, for instance by methods analogous to the preparation as disclosed in U.S. Pat. No. 4,540,780. A suitable method of production is the condensation of 4-bis-(2-, 3-, or 4-fluorophenyl)methylene piperidine or a salt thereof (for instance the hydrochloride), the synthesis of which is disclosed in U.S. Pat. No. 4,540,780, with 1-(4-halo-1-oxobutyl)pyrrolidine (n=1) or 1-(4-halo-1-oxobutyl)piperidine (n=2), wherein halo is a suitable halogen atom such as chlorine, bromine or iodine, after which the compound obtained is optionally converted into a pharmaceutically acceptable salt.

The novel compounds of the invention may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methane-sulphonic acid, fumaric acid, succinic acid, tartaric acid, citric acid, benzoic acid, and ascorbic acid.

The compounds of the invention may be administered enterally or parenterally, and for humans preferably in a daily dosage of 0,001–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

EXAMPLE 1

Preparation of 1-(triphenylmethyl)-4-piperidinecarboxylic acid ethylester

A solution of ethyl isonipecotate (25 g; 0.165 mol) in dichloromethane (250 ml) and triethylamine (50 ml) was cooled in a water bath and triphenylmethyl chloride (48.7 g; 0.175 mol) was added portionwise. Shortly after the addition was completed a precipitate was formed. The mixture was stirred at room temperature for 24 h and the mixture was then washed with water, dried over sodium sulfate and evaporated to dryness to give a yellow oil (74.0 g). This oil was triturated with methanol to give the product as cream coloured crystals in 97% yield (61.9 g); m.p. 164° C.

Preparation of α,α-bis-(4-fluorophenyl-1-(triphenylmethyl)-4-piperidinemethanol

1-Bromo4-fluorobenzene (154 ml; 1.402 mol) in anhydrous ether (640 ml) was added to a suspension of magnesium turnings (34.1 g; 1.404 mol) in anhydrous ether (250 ml) and the mixture was stirred under nitrogen, at a rate which gave a gentle reflux. The solution was cooled, stirred at room temperature for 45 min and then cooled in an ice bath. To this solution was added dropwise over 40 min. a solution of 1-(triphenylmethyl)-4-piperidinecarboxylic acid ethylester (90 g; 0.225 mol) in anhydrous tetrahydrofuran (1.2 l). After 1 h the cooling bath was removed and the reaction was allowed to stand at room temperature overnight. The reaction mixture was then heated under reflux for 30 min, poured into ice-water and the product was extracted into ethyl acetate. The extract was filtered to remove insolubles, washed with water, dried over sodium sulfate and evaporated to yield an oil which on trituration with hot n-hexane gave the product as crystals (68.0 g); m.p. 243° C.

Preparation of 4-[bis-(4-fluorophenyl)-methylene]-piperidine hydrochloride salt

α,α-Bis-(4-fluorophenyl)-1-(triphenylmethyl)-4-piperidinemethanol (67 g; 0.123 mol) was dissolved in hydrochloric acid (1 l; 2 mol/l) and the solution was heated under reflux for 2 h. The solution was cooled, the precipitated solid was collected by filtration and suspended in anhydrous diethyl ether. The mixture was stirred for 1 h, filtered and the solid was crystallised from methanol/ether to give the product (28.3 g) as white crystals; m.p. 83° C.

Preparation of 1-[4-[4-[bis-(4-fluorophenyl)methylene]-1-piperidinyl-1-oxobutyl]-pyrrolidine hydrochloride salt A solution of 4-chlorobutyryl chloride (0.68 ml; 6,07 mmol) in anhydrous dichloromethane (10 ml) was added dropwise to an iced cooled and stirred solution of pyrrolidine (0.57 ml; 6.83 mmol) and triethylamine (1 ml) in anhydrous dichloromethane (10 ml). After 1 h water was added and the dichloromethane solution was separated, washed with water, dried over sodium sulfate and evaporated to dryness to give 1-(4-chloro-1-oxobutyl)-pyrrolidine, which together with 4-[bis-(4-fluorophenyl)methylene]-piperidine hydrochloride (2.0 g; 6.2 mmol) and potassium carbonate (2.15 g; 15.55 mmol) were dissolved in dimethylformamide and the mixture was heated at 100° C. for 2 h. The solution was poured into water and the product was extracted with diethyl ether. The organic extract was washed with water, dried over sodium sulfate and evaporated to dryness to give 1-[4-[4-[bis-(4-fluorophenyl)methylene]-1-piperidinyl-1-oxobutyl]-pyrrolidine as an orange-yellow gum (2.33 g). This product was dissolved in methanol, oxalic acid (0.73 g) was added and the solution was allowed to crystallise to give 1-[4-[4-[bis-(4-fluorophenyl)-methylene]-1-piperidinyl]-1-oxobutyl]-pyrrolidine ethanedioate salt. This material was recrystallised from methanol/ether to give material (0.85 g) which was re-converted to the free base and chromatographed on silica. Elution with dichloromethane/methanol gave pure material which was dissolved in ether and treated with hydrogen chloride gas. The precipitate was crystallised from methanol/ether to give 1-[4-[4-[bis-(4-fluorophenyl)methylene]-1-piperidinyl-1-oxobutyl]-pyrrolidine hydrochloride salt (0.40 g); m.p. 107° C.

Similarly the purified free base was dissolved in ether/methanol (55/3, v/v), and the stirred solution was treated with a solution of methanesulphonic acid (1.05 mole equiv.) in ether. The product precipitated as a gum which crystallised on stirring. After the addition of more ether the solid was filtered and dried to give 1-[4-[4-[bis-(4-fluorophenyl)methylene]-1-piperidinyl-1-oxobutyl]-pyrrolidine methanesulphonic acid salt; m.p. 157–158° C.

EXAMPLE 2

Preparation of 1-[4-[4-[bis-(4-fluorophenyl) methylene]-1-piperidinyl-1-oxobutyl]piperidine (E)- 2-butanedioate (1:1) salt 4-Chlorobutyryl chloride in dichlormethane was added to an ice cooled solution of piperidine (1.8 ml; 17.6 mmol) and triethylamine (2.5 ml) in dichloromethane (40 ml) under an atmosphere of nitrogen. The mixture was stirred for 5 min whilst being cooled, then stirred at ambient temperature for 3 h. The solution was washed with water, dried over sodium sulfate and evaporated to give 1-(4-chloro-1-oxobutyl) piperidine as a pale yellow oil (2.1 g).

A mixture of 4-[bis(4-fluorophenyl)-methylene] piperidine hydrochloride (3.5 g; 11 mmol), prepared as described in the previous example, the above 1-(4-chloro-1-oxobutyl)-piperidine (2.1 g; 11 mmol) and potassium carbonate (3.3 g; 24 mmol) in dimethylformamide (40 ml) were heated at 80° C. for 6 h and the reaction mixture was poured into water. The product was extracted with ether and the extract was washed with water, dried over sodium sulfate and evaporated to give a gum which was chromatographed on silica. Elution with dichlormethane/methanol/ammonia gave the product as the free base which was dissolved in ethyl acetate and a solution of fumaric acid (0.25 g) in methanol was added. The solution was allowed to stand at 5° C. till crystallisation occurred, the crystals formed were collected to give the product (0.88 g); m.p. 145° C.

EXAMPLE 3

Apomorphine Climbing Test In Mice

Mice treated with apomorphine HCl tend to adopt a vertical position along the wall of a wire mesh cylinder, standing or climbing. This climbing behaviour is supposed to be elicited by apomorphine-mediated stimulation of dopamine receptors. Many drugs affect the climbing behaviour, but dopamine antagonists generally inhibit it in doses not interfering with spontaneous motor activity and/or motor coordination in mice. Test compounds which modulate this climbing behaviour may have antipsychotic activity.

The various treatments are randomly distributed over the mice. Each experiment consists of 1+n treatment groups:

1 being a control group of 12 mice receiving apomorphine and vehicle subcutaneously or being a control group of 12 mice receiving apomorphine subcutaneously and vehicle orally; n being (usually 4) compound groups of 12 mice receiving apomorphine and test compound subcutaneously or being compound groups of 12 mice receiving apomorphine subcutaneously and test compound orally.

Experiments are performed in 3 runs of 20 mice each.

The mice are marked and weighed, test compound or vehicle is administered subcutaneously and the mice are placed in small Macrolon cages of 17×11×13 cm, 5 mice per cage, or test compound or vehicle is administered orally and the mice are placed in Macrolon cages of 29×11×13 cm, 5 mice per cage. After 30 min 0.75 mg/kg apomorphine HCl is administered subcutaneously in mice treated subcutaneously with vehicle or test compound, or 0.75 mg/kg apomorphine HCl is administered subcutaneously in mice treated orally with vehicle or test compound, and the mice are placed individually in a wire mesh cylinder (diameter 12 cm, height 14 cm). At 10 min after the treatment with apomorphine the climbing behaviour of each mouse is observed and expressed as a score, according to the following grade:

| | |
|---|---|
| 4 paws on the floor | score 0 |
| 1 or 2 paws holding the wall | score 1 |
| 3 or 4 paws holding the wall | score 2 |

At 20 min after the treatment with apomorphine the climbing behaviour is observed and scored again.

For each treatment group the mean score per mouse is determined. The score of the control group should be at least 1.0; if not, the trial is rejected. The final result per group is expressed as the percentage over the control group.

The results of this test for the present test compounds are denoted in Table I (subcutaneous administration of test compound) and Table II (oral administration of test compound).

We claim:

1. A diphenylmethylene piperidine compound of the formula

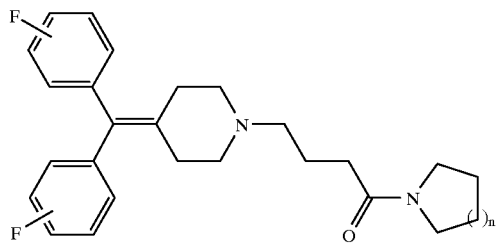

wherein n is 1 or 2; or a pharmaceutically acceptable salt thereof.

2. The diphenylmethylene piperidine compound of claim 1, wherein both fluorine atoms are attached to the para position of the benzene rings.

3. The diphenylmethylene piperidine compound of claim 1, having the formula

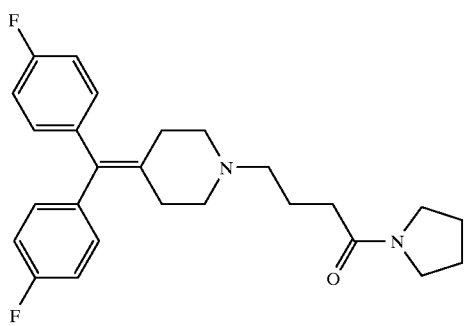

or a pharmaceutically acceptable salt thereof.

4. A pharmaceutical composition comprising the diphenylmethylene piperidine compound of claim 1, and pharmaceutically acceptable auxiliaries.

5. A method of preparation of the diphenylmethylene piperidine compound of claim 1, wherein 4-bis-(2-, 3-, or 4-fluorophenyl)methylene piperidine or a salt thereof is condensed with 1-(4-halo-1-oxobutyl)pyrrolidine (n=1) or 1-(4-halo-1-oxobutyl)-piperidine (n=2), wherein halo is a suitable halogen atom such as chlorine, bromine or iodine, after which the compound obtained is optionally converted into a pharmaceutically acceptable salt.

6. A method for the treatment of a psychotic disorder in a patient, comprising administering an effective amount of a diphenylmethylene piperidine compound of claim 1.

7. A method of preparing a pharmaceutical composition, comprising admixing a diphenylmethylene piperidine compound of claim 1 with one or more pharmaceutically acceptable auxiliaries.

* * * * *